US006980871B1

(12) United States Patent
Sweat

(10) Patent No.: US 6,980,871 B1
(45) Date of Patent: Dec. 27, 2005

(54) METHOD FOR PROVIDING A RADIATION FILTER FOR A RADIATION TREATMENT MACHINE

(75) Inventor: Richard L. Sweat, Longwood, FL (US)

(73) Assignee: .decimal, Inc., Sanford, FL (US)

( * ) Notice: Subject to any disclaimer, the term of this patent is extended or adjusted under 35 U.S.C. 154(b) by 0 days.

(21) Appl. No.: 10/892,652

(22) Filed: Jul. 16, 2004

(51) Int. Cl.[7] ................................................ G06F 19/00
(52) U.S. Cl. ......................... 700/97; 700/182; 378/156
(58) Field of Search ............................ 700/95–97, 182; 706/919; 378/156, 159

(56) References Cited

U.S. PATENT DOCUMENTS

| | | | | |
|---|---|---|---|---|
| 5,014,290 A * | 5/1991 | Moore et al. | ............... | 378/145 |
| 6,222,544 B1 * | 4/2001 | Tarr et al. | .................. | 715/839 |
| 6,381,304 B1 * | 4/2002 | Shoenfeld et al. | ............ | 378/65 |
| 2002/0006182 A1 * | 1/2002 | Kim et al. | .................... | 378/65 |

OTHER PUBLICATIONS

Medicalibration, Solid-IMRT®, Solid Solutions to Intensity Modulation in Radiation Therapy, available at www.solid-imrt.com.

* cited by examiner

*Primary Examiner*—Zoila Cabrera
(74) *Attorney, Agent, or Firm*—Allen, Dyer, Doppelt, Milbrath & Gilchrist, P.A.

(57) ABSTRACT

A method for providing a radiation filter for a radiation treatment machine includes receiving via e-mail design data for the radiation filter, and comparing the received design data to a radiation filter blank database for selecting a radiation filter blank compatible with the radiation treatment machine from a plurality of radiation filter blanks. The method further includes defining tooling instructions for the selected radiation filter blank, and programming a tooling machine based upon the defined tooling instructions. The programmed tooling machine is operated for machining the selected radiation filter blank into the radiation filter.

35 Claims, 6 Drawing Sheets

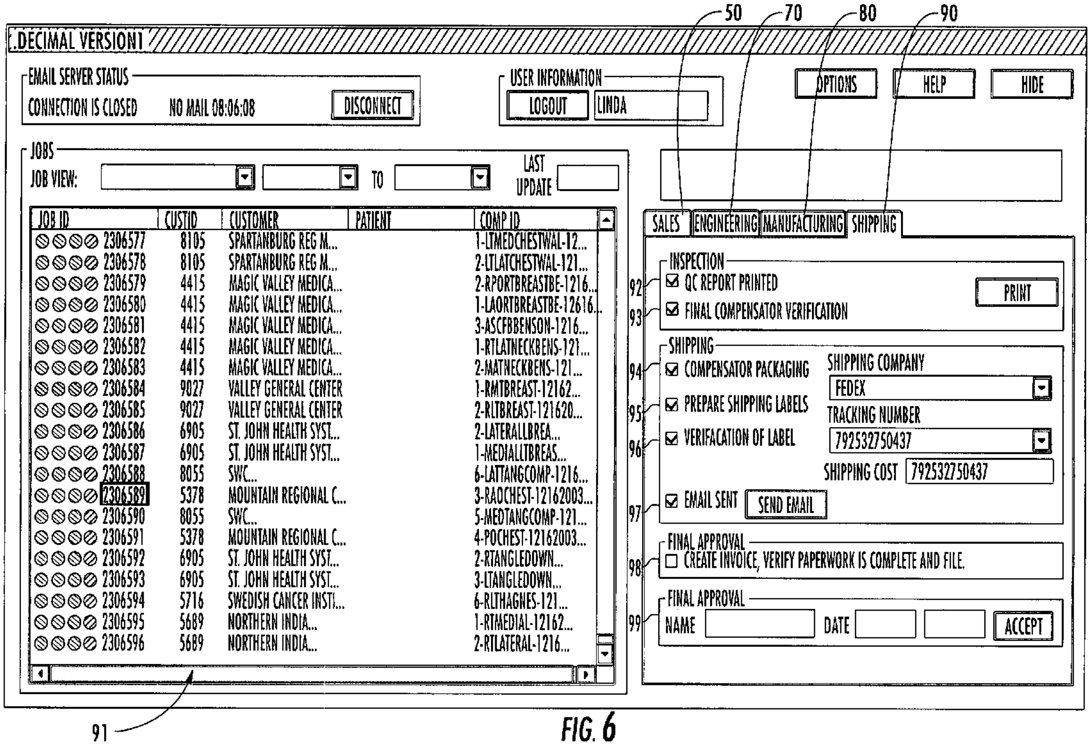

| JOB ID | CUSTID | CUSTOMER | PATIENT | COMP ID |
|---|---|---|---|---|
| 2306577 | 8105 | SPARTANBURG REG M... | | 1-LTMEDCHESTWAL-12... |
| 2306578 | 8105 | SPARTANBURG REG M... | | 2-LTLATCHESTWAL-121... |
| 2306579 | 4415 | MAGIC VALLEY MEDICA... | | 2-RPORTBREASTBE-1216... |
| 2306580 | 4415 | MAGIC VALLEY MEDICA... | | 1-LAORTBREASTBE-12616... |
| 2306581 | 4415 | MAGIC VALLEY MEDICA... | | 3-ASCFBBENSON-1216... |
| 2306582 | 4415 | MAGIC VALLEY MEDICA... | | 1-RTLATNECKBENS-121... |
| 2306583 | 4415 | MAGIC VALLEY MEDICA... | | 2-MATNECKBENS-121... |
| 2306584 | 9027 | VALLEY GENERAL CENTER | | 1-RMTBREAST-12162... |
| 2306585 | 9027 | VALLEY GENERAL CENTER | | 2-RLTBREAST-121620... |
| 2306586 | 6905 | ST. JOHN HEALTH SYST... | | 2-LATERALLBREA... |
| 2306587 | 6905 | ST. JOHN HEALTH SYST... | | 1-MEDIALLTBREAS... |
| 2306588 | 8055 | SWC... | | 6-LATTANGCOMP-1216... |
| 2306589 | 5378 | MOUNTAIN REGIONAL C... | | 3-RADCHEST-12162003... |
| 2306590 | 8055 | SWC... | | 5-MEDTANGCOMP-121... |
| 2306591 | 5378 | MOUNTAIN REGIONAL C... | | 4-POCHEST-12162003... |
| 2306592 | 6905 | ST. JOHN HEALTH SYST... | | 2-RTANGLEDOWN... |
| 2306593 | 6905 | ST. JOHN HEALTH SYST... | | 3-LTANGLEDOWN... |
| 2306594 | 5716 | SWEDISH CANCER INSTI... | | 6-RLTHAGNES-121... |
| 2306595 | 5689 | NORTHERN INDIA... | | 1-RTMEDIAL-12162... |
| 2306596 | 5689 | NORTHERN INDIA... | | 2-RTLATERAL-1216... |

FIG. 6

METHOD FOR PROVIDING A RADIATION FILTER FOR A RADIATION TREATMENT MACHINE

FIELD OF THE INVENTION

The present invention relates to the field of radiation therapy, and in particular, to radiation filters used in radiation treatment machines providing intensity modulated radiation therapy (IMRT).

BACKGROUND OF THE INVENTION

Intensity modulated radiation therapy (IMRT) is a treatment method for cancer patients requiring radiation treatment. IMRT is an extremely precise method of treatment delivery where the radiation dose conforms to the target and avoids the surrounding critical structures. Rather than having a single large radiation beam pass through the body, with IMRT the treatment is delivered from various angles and the intensity of the radiation beam is varied across the treatment area.

The radiation is effectively broken up into thousands of tiny pencil-thin radiation beams. With millimeter accuracy, these beams enter the body from many angles and intersect on the cancer. This results in a high radiation dosage to the tumor and a lower radiation dose to the surrounding healthy tissues.

One method for modulating the intensity of the radiation beam is based upon moving a multi-leaf collimator (MLC) in and out of the radiation beam from the radiation treatment machine. An MLC comprises a plurality of thin width mechanical blades or leaves, which are individually controlled by miniature motors and mechanical drive linkages. A computer controls the miniature motors for driving the individual blades in and out to shape the radiation beam. An advantage of an MLC based IMRT treatment machine is that the same MLC can be automatically controlled to support the individual needs of each patient receiving radiation treatment. In other words, the MLC is reconfigured for each new patient. Unfortunately, the cost for an MLC can easily exceed a half million dollars.

A more cost effective method for modulating the intensity of the radiation beam is based upon the use of a compensator. The compensator (also referred to herein as a radiation filter) used by the radiation therapy machine is specifically designed for that patient. The cost of such a filter is less than a couple of hundred dollars.

A compensator type radiation filter is machined from a solid piece of material (referred to herein as a radiation filter blank), and is mounted directly in the path of the radiation beam. The unique three-dimensional geometry of each machined radiation filter provides the conformal radiation dose distributions required by the cancer patient.

Since each radiation filter must be individually machined from a radiation filter blank, a compensator type radiation filter cannot be reused on other cancer patients. The radiation filter may be machined in-house by a radiation treatment center, or alternatively, it may be ordered from an outside machine shop.

Once an order is received by an outside machine shop, a number of information related tasks need to be performed before a radiation filter blank is actually machined into a radiation filter. For example, modeling and programming functions need to be determined. In addition, for each radiation filter machined, it must be properly labeled and verified for accuracy. Consequently, each order for a radiation filter requires a considerable amount of employee intervention before the filter is actually packaged and shipped.

One example of an outside machine shop providing radiation filters of this type is Medicalibration located in Ripon, Calif. Medicalibration receives orders via e-mail, wherein the e-mail includes design data for the radiation filter. Once the design data is received, the above noted steps are to be performed before the filter is packaged and shipped. If the number of orders being processed on a daily basis is small, then the required employee intervention is not a limiting factor. In contrast, if the number of orders being processed on a daily basis is large, then the required employee intervention can be a limiting factor.

SUMMARY OF THE INVENTION

In view of the foregoing background, it is therefore an object of the present invention to reduce the amount of employee intervention required by an outside machine shop when providing a radiation filter for a radiation treatment machine.

This and other objects, advantages and features in accordance with the present invention are provided by a method for providing a radiation filter for a radiation treatment machine, wherein the method comprises receiving via e-mail design data for the radiation filter, and comparing the received design data to a radiation filter blank database for selecting a radiation filter blank compatible with the radiation treatment machine from a plurality of radiation filter blanks. The method further comprises defining tooling instructions for the selected radiation filter blank, and programming a tooling machine based upon the defined tooling instructions. The programmed tooling machine is operated for machining the selected radiation filter blank into the radiation filter.

An advantage of comparing the received design data to the radiation filter blank database is that this may be done without employee intervention, i.e., it may be done via software. Each radiation filter blank in the radiation filter blank database corresponds to at least one particular type radiation treatment machine.

Each type radiation treatment machine may have a radiation filter size requirement, and compatibility of the selected radiation filter blank is based upon meeting the radiation filter size requirement of the intended radiation treatment machine. The radiation filter size requirement may correspond to a diameter of the radiation filter blank, and/or a thickness of the radiation filter blank. Each type radiation treatment machine may also have a radiation filter mounting requirement, and compatibility of the selected radiation filter blank is also based upon meeting the radiation filter mounting requirement of the intended radiation treatment machine. This particular feature in accordance with the present invention advantageously reduces employee intervention by using the radiation filter blank database for selecting a radiation filter blank compatible with the intended radiation treatment machine.

The method may further comprise comparing the received design data with a radiation filter database comprising design data of previously machined radiation filters to avoid duplicating the radiation filter. The radiation filter database may comprise a cyclic redundancy check (CRC) number for each of the previously machined radiation filters. The comparing may comprise generating a CRC number for the received design data, and then comparing the generated CRC number with the CRC numbers in the radiation filter database. This particular feature in accordance with the present invention advantageously reduces employee intervention by using the radiation filter database for determining if the radiation filter has already been machined.

Defining the tooling instruction may comprise comparing the received design data to a tooling database comprising a plurality of tooling strategies, with the tooling instructions being defined based upon the tooling strategies in the tooling database. Each tooling strategy in the tooling database may comprise at least one end-mill associated therewith to be used by the tooling machine. Each tooling strategy may be defined based upon a size of the radiation filter blank, a thickness of the radiation filter and a material composition (e.g., brass or aluminum) of the radiation filter blank.

The tooling instructions may further comprise engraving an identification number in a predetermined location on the radiation filter blank, with the identification number being assigned based on a database of previously assigned serial numbers and on the received design data. Since the identification number is assigned automatically, errors are no longer introduced as a result of employee intervention.

The method may further comprise measuring a plurality of inspection points on the radiation filter after machining, defining an inspection database based upon the plurality of measured inspection points and the received design data, and generating a quality assurance report based upon the defined inspection database. This particular feature in accordance with the present invention advantageously reduces employee intervention by using the inspection database for generating the quality assurance report. The method further comprises shipping the radiation filter, and sending confirmation via e-mail that the radiation filter has been shipped.

Another aspect of the present invention is directed to a computer-readable medium having stored thereon a data structure comprising a first data field containing data for receiving an e-mail providing design data for a radiation filter to be used with a radiation treatment machine, and a second data field containing data for comparing the received design data to a radiation filter blank database for selecting a radiation filter blank compatible with the radiation treatment machine from a plurality of radiation filter blanks.

A third data field contains data for defining tooling instructions for the selected radiation filter blank, and a fourth data field contains data for programming a tooling machine based upon the defined tooling instructions. A fifth data field contains data for operating the tooling machine for machining the selected radiation filter blank into the radiation filter.

BRIEF DESCRIPTION OF THE DRAWINGS

FIGS. 3–6 are user interface displays for processing a received order for a radiation filter in accordance with the present invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
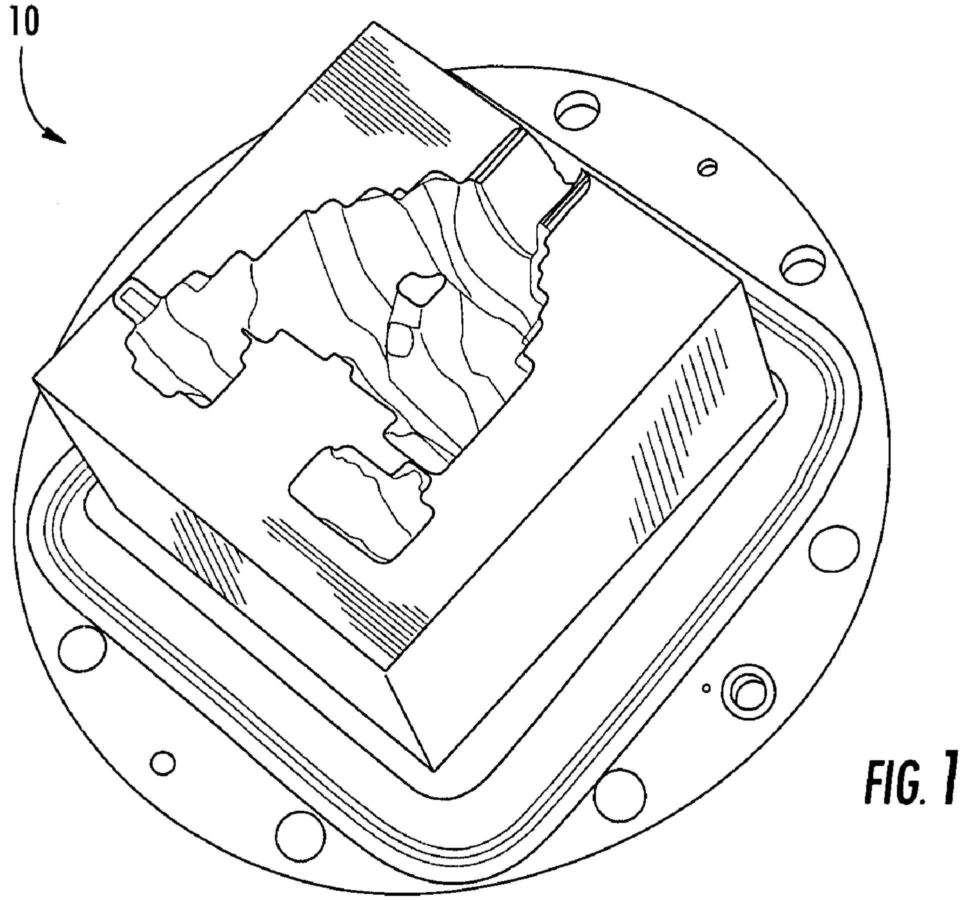
FIG. 1 is a perspective view of a radiation filter to be used in a radiation treatment machine in accordance with the present invention.

Referring initially to FIG. 1, the present invention is directed to a method for providing a radiation filter 10 for a radiation treatment machine. The illustrated radiation filter 10 is also known as a compensator or as a modulator, and is machined from a solid piece of material. This solid piece of material may be aluminum or brass, for example, and is commonly referred to as a blank. A blank will also be referred to as a radiation filter blank.

As discussed above, measurement technology at radiation treatment planning centers can determine precise three-dimensional coordinates for a cancerous tumor along with precise locations and densities for the healthy bone and tissue surrounding it. This design data makes it possible to design a radiation filter 10 for a radiation treatment machine that uses variations in the thickness of the metal to vary the intensity of the radiation, thus producing a radiation field conforming to the topography of the patient.

Figure 2:
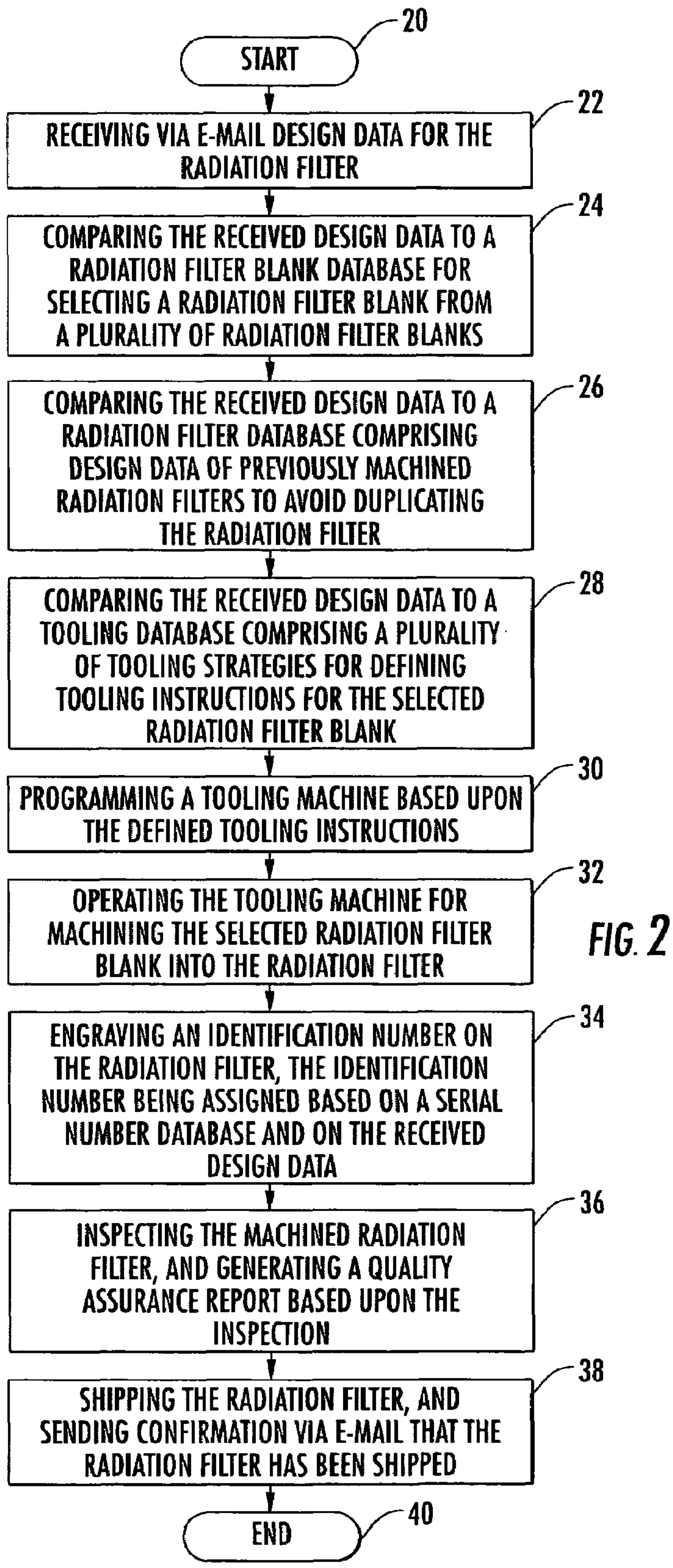
FIG. 2 is a flow chart illustrating a method for providing a radiation filter for a radiation treatment machine in accordance with the present invention.

Referring now to FIG. 2, a flow chart illustrating a method for providing a radiation filter 10 in accordance with the present invention will now be discussed. From the start (Block 20), the method comprises receiving via e-mail design data for the radiation filter 10 at Block 22, and comparing the received design data to a radiation filter database for selecting a radiation filter blank compatible with the radiation treatment machine from a plurality of radiation filter blanks at Block 24.

Each radiation filter blank in the radiation filter blank database corresponds to a particular type radiation treatment machine. Each type radiation treatment machine has a particular radiation filter size requirement, and compatibility of the selected radiation filter blank is based upon meeting the radiation filter size requirement of the intended radiation treatment machine. The radiation filter size requirement corresponds to a diameter of the radiation filter blank, and to a thickness of the radiation filter blank. The thickness of the radiation filter bank for any particular radiation treatment machine typically includes more than one value, such as ½ or 1 inch. The actual value selected will be determined based upon the design data for the radiation filter.

In addition, each type radiation treatment machine also has a radiation filter mounting requirement, and compatibility of the selected radiation filter blank is also based upon meeting the radiation filter mounting requirement of the intended radiation treatment machine. This particular feature of the present invention advantageously reduces employee intervention by using the radiation filter blank database for selecting the radiation filter blank compatible with the intended radiation treatment machine.

The method further comprises comparing at Block 26 the design data of the radiation filter 10 with a radiation filter database comprising design data of previously machined radiation filters to avoid duplicating the radiation filter 10. The radiation filter database comprises a cyclic redundancy check (CRC) number for each of the previously machined radiation filters. The comparing comprises generating a CRC number for the received design data, and then comparing the generated CRC number with the CRC numbers in the radiation filter database. In the event that two CRC numbers match, then a very high probability exists that the radiation filter has already been machined. This particular feature advantageously reduces employee intervention by using the radiation filter database for preventing duplicate orders.

The tooling instructions for the selected radiation filter blank are defined at Block 28. The tooling machine may be a milling machine or a multi-spindle, live tooling lathe, for example. The cutting tools used by milling machines are commonly known as end-mills. Example milling machines include the Mazak 3-axis and the Mazak 5-axis milling machines. An example lathe is the Mazak multi-spindle lathe with live tooling. Depending on the received design data associated with the radiation filter 10, one or more end-mills may be selected.

Defining the tooling instructions comprises comparing the received design data to a tooling database comprising a plurality of tooling strategies. The tooling instructions are thus defined based upon the tooling strategies in the tooling database, as readily appreciated by those skilled in the art. Each tooling strategy in the tooling database comprises at least one end-mill associated therewith to be used by the tooling machine. This particular feature advantageously reduces employee intervention by using the tooling database for defining the tooling instructions.

Each tooling strategy in the tooling database comprises at least one end-mill associated therewith to be used by the tooling machine. Each tooling strategy is defined based upon a size of the radiation filter blank, a thickness of the radiation filter and a material composition (e.g., brass or aluminum) of the radiation filter blank.

The tooling machine is programmed at Block 30 based upon the defined tooling instructions. The method further comprises operating the tooling machine at Block 32 for machining the selected radiation filter blank into the radiation filter.

The method further comprises at Block 34 engraving an identification number in a predetermined location on the radiation filter blank. The identification number is assigned based on a database of previously assigned serial numbers and on the received design data. Since the identification number is assigned automatically, errors are no longer introduced as a result of employee intervention.

The unique identification number is engraved on a flat area of the radiation filter 10 that is separate from the machined three-dimensional area. The identification number includes a serial number, a beam number and description as determined based upon the received design data, and the date. This particular feature also advantageously reduces employee intervention by determining via software where to engrave the identification number, and by determining the identification number. Moreover, errors in determining the identification number are significantly reduced since employee intervention is not required for determining the identification number.

The machined radiation filter 10 is inspected and a quality assurance report based upon the inspection is generated at Block 36. Generating the quality assurance report is based upon measuring a plurality of inspection points on the radiation filter 10 after machining, and defining an inspection database based upon the plurality of measured inspection points and the received design data. The quality assurance report is generated based upon the defined inspection database. This particular feature in accordance with the present invention also advantageously reduces employee intervention by using the inspection database for generating the quality assurance report.

Provided the quality assurance report is satisfactory, then the radiation filter 10 is shipped and confirmation via e-mail is sent at Block 38 confirming that the radiation filter has been shipped. The confirmation e-mail also includes a tracking number associated with the shipped radiation filter 10. The method ends at Block 30.

An illustrated embodiment of display formats on a computer screen for processing and tracking a received e-mail for a radiation filter 10 will now be described with reference to FIGS. 3–6. Tracking the received e-mail is divided into four separate sections: sales 50, engineering 70, manufacturing 80 and shipping 90. Each of the four sections is represented by a tab, and selection of any particular tab causes the corresponding display screen to be displayed.

Figure 3:
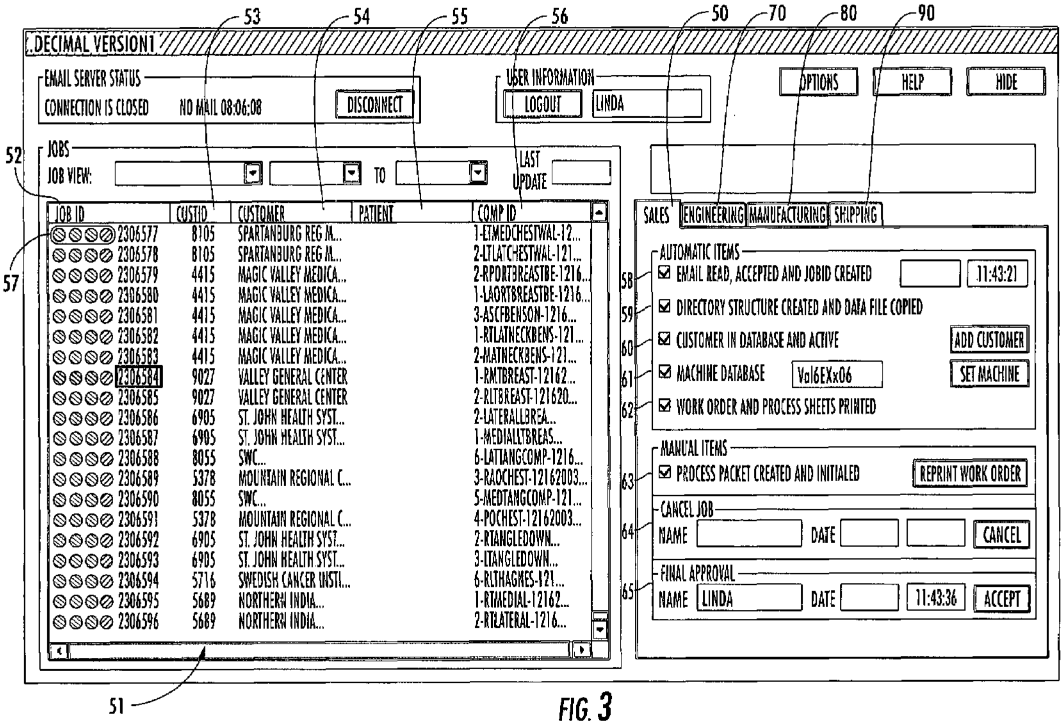

The sales tab 50 tab is selected in FIG. 3, and display field 51 provides a job number 52 for each order along with the customer identification number 53, the customer 54 placing the order, the patient's name 55 and the compiled identification 56 for the corresponding radiation filter. Four circles 57 are also associated with each job number 52. The four circles 57 correspond to the four sections: sales 50, engineering 70, manufacturing 80 and shipping 90. An open or light colored circle indicates that the corresponding section has not yet been completed. If the corresponding section has been completed, then the appropriate circle 57 is closed or shaded in.

Still referring to FIG. 3, the sales tab 50 provides a field 58 indicating that the e-mail was read and accepted, and a job identification number 52 was created. Field 59 indicates that a directory structure was created, and the design data has been copied into the directory. Field 60 indicates that the customer placing the order is in a customer database, and field 61 indicates that the radiation therapy machine intending to use the radiation filter 10 is in a radiation therapy machine database. If the radiation therapy machine is not in the radiation therapy machine database, then an error message is generated. Consequently, new data corresponding to this particular radiation therapy machine is entered into the database so that the process may continue. Field 62 indicates that a work order and process sheets have been printed. Field 63 can be selected if the work order and process sheets need to be reprinted. Field 64 can be selected if the order needs to be cancelled. Approval of the items corresponding to the sales tab 50 is provided in field 65.

Figure 4:
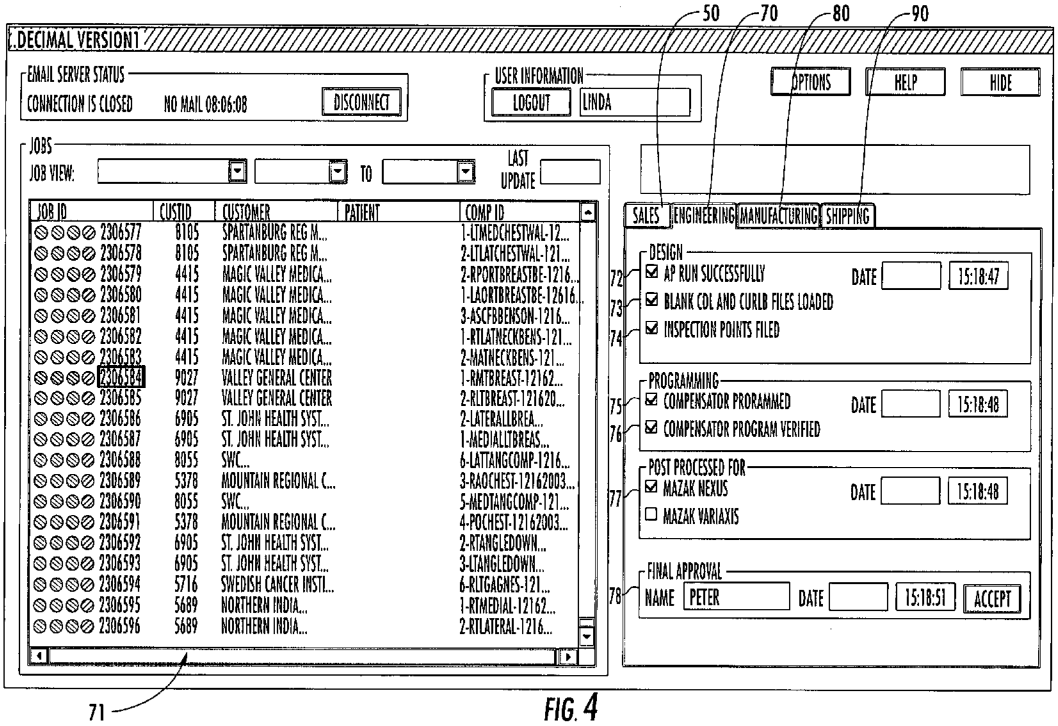

The engineering tab 70 is selected in FIG. 4, and display field 71 repeats the same information as in field 51. Field 72 indicates if the API has been successfully run. The API reads the customer's software providing the design data. Field 73 indicates that a radiation filter blank has been selected. Field 74 indicates that inspection points for the radiation filter 10 have been verified. Field 75 indicates that the radiation filter 10 has been programmed, and field 76 indicates that the radiation filter program has been verified. Verification is performed based upon generating a simulated radiation filter 10, as readily appreciated by those skilled in the art. Field 77 indicates for which machine the post processed file will be sent to. Approval of the items corresponding to the engineering tab 70 is provided in field 78.

Figure 5:
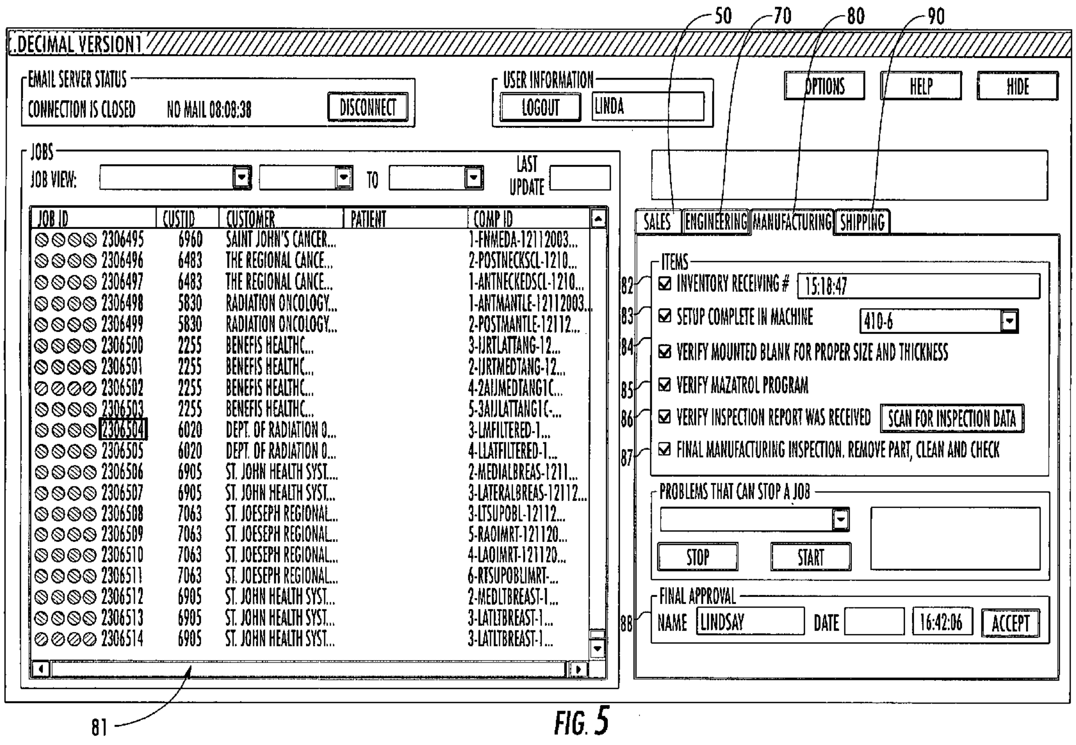

The manufacturing tab 80 is selected in FIG. 5, and display field 81 repeats the same information as in fields 51 and 71. Field 82 indicates if the inventory receiving number has been assigned. This number is traceable back to the vendor providing the alloy for the radiation filter blank. Field 83 indicates if the tooling machine has been setup. Field 84 indicates is the radiation filter blank is the proper size and thickness. Field 85 indicates that the tooling machine has been programmed. Field 86 indicates that an inspection report has been received. This is performed automatically after the radiation filter block has been machined into the desired radiation filter 10. Field 87 indicates that final inspection is complete, and that the radiation filter 10 has been removed, checked and cleaned. Approval of the items corresponding to the manufacturing tab 80 is provided in field 88.

The shipping tab 90 is selected in FIG. 6, and display field 91 repeats the same information as in fields 51, 71 and 81. Field 92 indicates that the quality assurance report has been printed. Field 93 indicates that the machined radiation filter 10 has been verified. Fields 94, 95 and 96 indicate that the radiation filter 10 has been packaged, a shipping label has been generated, and the shipping label has been verified with a tracking number. Field 97 indicates that confirmation e-mail has been sent to the customer ordering the radiation filter 10. The confirmation e-mail includes the shipping information. Field 98 indicates that an invoice has been completed. Approval of the items corresponding to the shipping tab 90 is provided in field 99.

Another aspect of the present invention is directed to a computer-readable medium having stored thereon a data structure comprising a first data field containing data for receiving an e-mail providing design data for a radiation filter 10 to be used with a radiation treatment machine, and a second data field containing data for comparing the received design data to a radiation filter blank database for selecting a radiation filter blank compatible with the radiation treatment machine from a plurality of radiation filter blanks.

A third data field contains data for defining tooling instructions for the selected radiation filter blank, and a fourth data field contains data for programming a tooling machine based upon the defined tooling instructions. A fifth data field contains data for operating the tooling machine for machining the selected radiation filter blank into the radiation filter 10.

Many modifications and other embodiments of the invention will come to the mind of one skilled in the art having the benefit of the teachings presented in the foregoing descriptions and the associated drawings. For example, the remote common passenger carrier check-in services may be provided at locations other than hotels, convention centers and resorts. In addition, the outside contractor personnel may also be able to issue/sell new tickets to travelers on a common passenger carrier. Therefore, it is to be understood that the invention is not to be limited to the specific embodiments disclosed, and that the modifications and embodiments are intended to be included within the scope of the dependent claims.

What is claimed is:

1. A method for providing a radiation filter for a radiation treatment machine, the method comprising:

receiving via e-mail design data for the radiation filter;

comparing the received design data to a radiation filter blank database for selecting a radiation filter blank compatible with the radiation treatment machine from a plurality of radiation filter blanks;

defining tooling instructions for the selected radiation filter blank;

programming a tooling machine based upon the defined tooling instructions; and operating the tooling machine for machining the selected radiation filter blank into the radiation filter.

2. A method according to claim 1 wherein each radiation filter blank in the radiation filter blank database corresponds to at least one particular type radiation treatment machine, each type radiation treatment machine having a radiation filter size requirement, and compatibility of the selected radiation filter blank is based upon meeting the radiation filter size requirement of the intended radiation treatment machine.

3. A method according to claim 2 wherein the radiation filter size requirement corresponds to a diameter of the radiation filter blank.

4. A method according to claim 2 wherein the radiation filter size requirement corresponds to at least one thickness of the radiation filter blank.

5. A method according to claim 2 wherein each type radiation treatment machine also has a radiation filter mounting requirement, and compatibility of the selected radiation filter blank is also based upon meeting the radiation filter mounting requirement of the intended radiation treatment machine.

6. A method according to claim 1 further comprising comparing the received design data with a radiation filter database comprising design data of previously machined radiation filters to avoid duplicating the radiation filter.

7. A method according to claim 6 wherein the radiation filter database comprises a cyclic redundancy check (CRC) number for each of the previously machined radiation filters; and wherein the comparing comprises generating a CRC number for the received design data, and then comparing the generated CRC number with the CRC numbers in the radiation filter database.

8. A method according to claim 1 wherein defining the tooling instructions comprises comparing the received design data to a tooling database comprising a plurality of tooling strategies, with the tooling instructions being defined based upon the tooling strategies in the tooling database.

9. A method according to claim 8 wherein each tooling strategy in the tooling database comprises at least one end-mill associated therewith to be used by the tooling machine.

10. A method according to claim 8 wherein each tooling strategy is defined based upon a size of the radiation filter blank, a thickness of the radiation filter and a material composition of the radiation filter blank.

11. A method according to claim 1 wherein the tooling instructions further comprise engraving an identification number in a predetermined location on the radiation filter blank, with the identification number being assigned based on a database of previously assigned serial numbers and on the received design data.

12. A method according to claim 1 further comprising:

measuring a plurality of inspection points on the radiation filter after machining;

defining an inspection database based upon the plurality of measured inspection points and the received design data; and generating a quality assurance report based upon the defined inspection database.

13. A method according to claim 1 further comprising:

shipping the radiation filter; and sending confirmation via e-mail that the radiation filter has been shipped.

14. A method for providing a radiation filter for a radiation treatment machine, the method comprising:

receiving via e-mail design data for the radiation filter;

comparing the received design data with a radiation filter database comprising design data of previously machined radiation filters to avoid duplicating the radiation filter;

comparing the received design data to a radiation filter blank database for selecting a radiation filter blank compatible with the radiation treatment machine from a plurality of radiation filter blanks;

comparing the received design data to a tooling database comprising a plurality of tooling strategies for defining tooling instructions for the selected radiation filter blank;

programming a tooling machine based upon the defined tooling instructions; and operating the tooling machine for machining the selected radiation filter blank into the radiation filter.

15. A method according to claim 14 wherein each radiation filter blank in the radiation filter blank database corresponds to at least one particular type radiation treatment machine, each type radiation treatment machine having a radiation filter size requirement, and compatibility of the selected radiation filter blank is based upon meeting the radiation filter size requirement of the intended radiation treatment machine.

16. A method according to claim 15 wherein the radiation filter size requirement corresponds to at least one of a diameter and a thickness of the radiation filter blank.

17. A method according to claim 15 wherein each type radiation treatment machine also has a radiation filter mounting requirement, and compatibility of the selected radiation filter blank is also based upon meeting the radiation filter mounting requirement of the intended radiation treatment machine.

18. A method according to claim 14 wherein the radiation filter database comprises a cyclic redundancy check (CRC) number for each of the previously machined radiation filters; and wherein the comparing comprises generating a CRC number for the received design data, and then comparing the generated CRC number with the CRC numbers in the radiation filter database.

19. A method according to claim 14 wherein each tooling strategy in the tooling database comprises at least one end-mill associated therewith to be used by the tooling machine.

20. A method according to claim 14 wherein each tooling strategy is defined based upon a size of the radiation filter blank, a thickness of the radiation filter and a material composition of the radiation filter blank.

21. A method according to claim 14 wherein the tooling instructions further comprise engraving an identification number in a predetermined location on the radiation filter blank, with the identification number being assigned based on a database of previously assigned serial numbers and on the received design data.

22. A method according to claim 14 further comprising:

measuring a plurality of inspection points on the radiation filter after machining;

defining an inspection database based upon the plurality of measured inspection points and the received design data; and generating a quality assurance report based upon the defined inspection database.

23. A method according to claim 14 further comprising:

shipping the radiation filter; and sending confirmation via e-mail that the radiation filter has been shipped.

24. A computer-readable medium having stored thereon a data structure comprising:

a first data field containing data for receiving an e-mail providing design data for a radiation treatment machine;

a second data field containing data for comparing the received design data to a radiation filter blank database for selecting a radiation filter blank compatible with the radiation treatment machine from a plurality of radiation filter blanks;

a third data field containing data for defining tooling instructions for the selected radiation filter blank;

a fourth data field containing data for programming a tooling machine based upon the defined tooling instructions; and a fifth data field containing data for operating the tooling machine for machining the selected radiation filter blank into the radiation filter.

25. A computer-readable medium according to claim 24 wherein each radiation filter blank in the radiation filter blank database corresponds to at least one particular type radiation treatment machine, each type radiation treatment machine having a radiation filter size requirement, and compatibility of the selected radiation filter blank is based upon meeting the radiation filter size requirement of the intended radiation treatment machine.

26. A computer-readable medium according to claim 25 wherein the radiation filter size requirement corresponds to at least one of a diameter and a thickness of the radiation filter blank.

27. A computer-readable medium according to claim 25 wherein each type radiation treatment machine also has a radiation filter mounting requirement, and compatibility of the selected radiation filter blank is also based upon meeting the radiation filter mounting requirement of the intended radiation treatment machine.

28. A computer-readable medium according to claim 24 further comprising a sixth data field containing data for comparing the received design data with a radiation filter database comprising design data of previously machined radiation filters to avoid duplicating the radiation filter.

29. A computer-readable medium according to claim 28 wherein the radiation filter database comprises a cyclic redundancy check (CRC) number for each of the previously machined radiation filters; and wherein the sixth data field further comprises data for generating a CRC number for the received design data, and then comparing the generated CRC number with the CRC numbers in the radiation filter database.

30. A computer-readable medium according to claim 24 wherein the third data field for defining the tooling instructions further comprises data for comparing the received design data to a tooling database comprising a plurality of tooling strategies, with the tooling instructions being defined based upon the tooling strategies in the tooling database.

31. A computer-readable medium according to claim 30 wherein each tooling strategy in the tooling database comprises at least one end-mill associated therewith to be used by the tooling machine.

32. A computer-readable medium according to claim 30 wherein each tooling strategy is defined based upon a size of the radiation filter blank, a thickness of the radiation filter and a material composition of the radiation filter blank.

33. A computer-readable medium according to claim 24 wherein the tooling instructions in the third database further comprise instructions for engraving an identification number in a predetermined location on the radiation filter blank, with the identification number being assigned based on a database of previously assigned serial numbers and on the received design data.

34. A computer-readable medium according to claim 24 further comprising:

a seventh data field containing data for measuring a plurality of inspection points on the radiation filter after machining;

an eighth data field containing data for defining an inspection database based upon the plurality of measured inspection points and the received design data; and a ninth data field containing data for generating a quality assurance report based upon the inspection database.

35. A computer-readable medium according to claim 24 further comprising:

a tenth data field containing data for generating a shipping label for shipping the radiation filter; and an eleventh data field containing data for sending confirmation via e-mail that the radiation filter has been shipped.

* * * * *

UNITED STATES PATENT AND TRADEMARK OFFICE

CERTIFICATE OF CORRECTION

PATENT NO. : 6,980,871 B1

DATED : December 27, 2005

INVENTOR(S) : Sweat

It is certified that error appears in the above-identified patent and that said Letters Patent is hereby corrected as shown below:

<u>Column 4,</u>
Line 43, delete “bank” and insert -- blank --.

<u>Column 6,</u>
Line 4, delete “30” and insert -- 40 --.
Line 63, delete “is” and insert -- if --.

<u>Column 7,</u>
Lines 39-44, delete “For example, the remote common passenger carrier check-in services may be provided at locations other than hotels, convention centers and resorts. In addition, the outside contractor personnel may also be able to issue/sell new tickets to travelers on a common passenger carrier.”.

Signed and Sealed this

Second Day of May, 2006

JON W. DUDAS

*Director of the United States Patent and Trademark Office*